United States Patent
Tanghal (10) Patent No.: US 11,364,089 B2
(45) Date of Patent: Jun. 21, 2022

(54) MARKER DELIVERY DEVICE AND METHOD OF DEPLOYING A MARKER

(71) Applicant: Devicor Medical Products, Inc., Cincinnati, OH (US)

(72) Inventor: Emmanuel Tanghal, Mason, OH (US)

(73) Assignee: Devicor Medical Products, Inc., Cincinnati, OH (US)

(*) Notice: Subject to any disclaimer, the term of this patent is extended or adjusted under 35 U.S.C. 154(b) by 986 days.

(21) Appl. No.: 15/977,186

(22) Filed: May 11, 2018

(65) Prior Publication Data

US 2018/0318037 A1 Nov. 8, 2018

Related U.S. Application Data

(63) Continuation of application No. PCT/US2016/061180, filed on Nov. 9, 2016.

(60) Provisional application No. 62/254,597, filed on Nov. 12, 2015.

(51) Int. Cl.
*A61B 90/00* (2016.01)
*A61B 10/02* (2006.01)

(52) U.S. Cl.
CPC .......... *A61B 90/39* (2016.02); *A61B 10/0233* (2013.01); *A61B 2090/3908* (2016.02); *A61B 2090/3987* (2016.02)

(58) Field of Classification Search
CPC ..................................................... A61B 90/39
See application file for complete search history.

(56) References Cited

U.S. PATENT DOCUMENTS

| | | | |
|---|---|---|---|
| 5,526,822 A | 6/1996 | Burbank et al. | |
| 5,879,357 A * | 3/1999 | Heaton | A61B 90/39 606/116 |
| 5,928,164 A | 7/1999 | Burbank et al. | |
| 6,017,316 A | 1/2000 | Ritchart et al. | |
| 6,086,544 A | 7/2000 | Hibner et al. | |
| 6,162,187 A | 12/2000 | Buzzard et al. | |
| 6,228,055 B1 | 5/2001 | Foerster et al. | |
| 6,371,904 B1 | 4/2002 | Sirimanne et al. | |
| 6,432,065 B1 | 8/2002 | Burdorff et al. | |
| 6,471,700 B1 * | 10/2002 | Burbank | A61B 10/0266 600/562 |
| 6,626,849 B2 | 9/2003 | Huitema et al. | |
| 6,752,768 B2 | 6/2004 | Burdorff et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |

(Continued)

OTHER PUBLICATIONS

International Search Report and Written Opinion dated Feb. 13, 2017 for Application No. PCT/US2016/061180, 8 pgs.

(Continued)

*Primary Examiner* — Joseph M Santos Rodriguez
(74) *Attorney, Agent, or Firm* — Frost Brown Todd LLC (57) ABSTRACT

A marker delivery device is described and claims. The marker delivery device is used to implant a detectable marker after a biopsy procedure is performed. The marker delivery device includes a cannula comprising a distal end and a marker exit positioned proximate the distal end; an actuator movable to a marker deployment position, wherein the actuator is slidably disposed within the cannula; and a retainment mechanism configured to retain the actuator in the deployment position.

16 Claims, 9 Drawing Sheets

(56) References Cited

U.S. PATENT DOCUMENTS

| | | | |
|---|---|---|---|
| 7,047,063 B2 | 5/2006 | Burbank et al. |
| 7,229,417 B2 | 6/2007 | Foerster et al. |
| 7,442,171 B2 | 10/2008 | Stephens et al. |
| 7,465,279 B2 | 12/2008 | Beckman et al. |
| 7,648,466 B2 | 1/2010 | Stephens et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,068,895 B2 | 11/2011 | Speeg et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,241,299 B2 | 8/2012 | Hibner |
| 8,251,916 B2 | 8/2012 | Speeg et al. |
| 8,371,443 B2 | 2/2013 | Nock et al. |
| 8,414,602 B2 | 4/2013 | Selis |
| 8,454,531 B2 | 6/2013 | Speeg et al. |
| 8,532,747 B2 | 9/2013 | Nock et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 2006/0074345 A1 | 4/2006 | Hibner |
| 2007/0010738 A1 | 1/2007 | Mark et al. |
| 2008/0033280 A1* | 2/2008 | Lubock | A61B 90/39 600/414 |
| 2009/0131821 A1 | 5/2009 | Speeg et al. |
| 2009/0192408 A1 | 7/2009 | Mark |
| 2010/0152610 A1 | 6/2010 | Parihar et al. |
| 2010/0160819 A1 | 6/2010 | Parihar et al. |
| 2013/0237912 A1 | 9/2013 | Speeg |
| 2013/0324882 A1 | 12/2013 | Mescher |
| 2014/0276037 A1 | 9/2014 | Johnson et al. |

OTHER PUBLICATIONS

U.S. Appl. No. 62/254,597, entitled "Marker Delivery Device and Method of Deploying a Marker," filed Nov. 12, 2015.

\* cited by examiner

MARKER DELIVERY DEVICE AND METHOD OF DEPLOYING A MARKER

RELATED APPLICATION

The present application for patent claims priority to U.S. Provisional Application No. 62/254,597 entitled "MARKER DELIVERY DEVICE AND METHOD OF DEPLOYING A MARKER" filed Nov. 12, 2015, which is assigned to the assignee hereof, and incorporated herein by reference in its entirety.

FIELD OF THE INVENTION

The present invention relates generally to marker delivery devices and methods of deploying a marker.

BACKGROUND OF THE INVENTION

Biopsy samples have been obtained in a variety of ways in various medical procedures using a variety of devices. Biopsy devices may be used under stereotactic guidance, ultrasound guidance, Magnetic Resonance Imaging (MRI) guidance, Positron emission mammography (PEM) guidance, Breast Specific Gamma Imaging (BSGI) guidance, or otherwise.

Example biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 30, 2003; U.S. Pat. No. 7,442,171, entitled "Remote Thumbwheel for a Surgical Biopsy Device," issued Oct. 28, 2008; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pat. No. 9,095,326, entitled "Biopsy System with Vacuum Control Module," issued Aug. 4, 2015; U.S. Pat. No. 8,251,916, entitled "Revolving Tissue Sample Holder for Biopsy Device," issued Aug. 28, 2012; and U.S. Pat. No. 8,532,747, entitled "Biopsy Marker Delivery Device," issued Sep. 10, 2013. The disclosure of each of the above-cited U.S. patents and U.S. patent application Publications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, CORMARK™, HYDROMARK®, and MAMMOSTAR™ brand devices distributed by Devicor Medical Products, Inc. of Cincinnati, Ohio. Further example devices and methods for marking a biopsy site are disclosed in U.S. Pat. No. 7,465,279, entitled "Marker Device and Method of Deploying a Cavity Marker Using a Surgical Biopsy Device," issued Dec. 16, 2008; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002, U.S. Pub. No. 2014/0276037, entitled "Biopsy Site Marker Applier," published Sep. 18, 2004; U.S. Pub. No. 2013/0237912, entitled "Biopsy Marker Delivery Device," published Sep. 12, 2013; U.S. Pat. No. 8,371,443, entitled "Biopsy Marker Delivery Device," issued Sep. 10, 2013; U.S. Pat. No. 8,241,299, entitled "Biopsy Marker Delivery Configured to Retain Marker Prior to Intended Deployment," issued Aug. 14, 2012; U.S. Pat. No. 8,068,895, entitled "Biopsy Site Marker Deployment Instrument," issued Nov. 14, 2011; and U.S. Pat. No. 8,414,602, entitled "Biopsy Device and Methods," issued Apr. 9, 2013. The disclosure of each of the above-cited U.S. patents and U.S. patent application Publications is incorporated by reference herein.

However, when operating the above-described marker deployment devices, the operator is not provided with an adequate and reliable indication that the implantable marker has been fully deployed. Thus, there is a need in the art for a marker deployment system including a mechanism to ensure that the implantable marker is fully deployed from the delivery system.

SUMMARY OF THE INVENTION

Aspects of the present invention provide, among other variations, a marker delivery device including a cannula comprising a distal end and a marker exit positioned proximate the distal end, an actuator movable to a marker deployment position, wherein the actuator is slidably disposed within the cannula; and a retainment mechanism configured to retain the actuator in the deployment position.

In another aspect of the present invention, a method of deploying a marker includes translating an actuator within a cannula to a marker deployment position; retaining the actuator in the marker deployment position with a retainment mechanism, and expelling the marker out of a marker exit positioned proximate a distal end of the cannula.

Additional advantages and novel features of various aspects of the present invention will be set forth in part in the description that follows, and in part will become more apparent to those skilled in the art upon examination of the following or upon learning by practice thereof.

DETAILED DESCRIPTION

The following description of certain examples of the invention should not be used to limit the scope of the present invention. Other examples, features, aspects, embodiments, advantages, and at least one of the best modes contemplated for carrying out of the invention will become apparent to those skilled in the art from the following description, which is by way of illustration only, and in no way designed to limit the scope of the present invention. As will be realized, the present invention is capable of other different and obvious aspects, all without departing from the scope of the present invention. Accordingly, the drawings and descriptions should be regarded as illustrative in nature and not restrictive.

In an aspect of the present invention a marker delivery device includes a cannula comprising a distal end and a marker exit positioned proximate the distal end, an actuator movable to a marker deployment position, wherein the actuator is slidably disposed within the cannula, and a retainment mechanism configured to retain the actuator in the deployment position.

In another aspect of the present invention, a method of deploying a marker includes translating an actuator within a cannula to a marker deployment position; retaining the actuator in the marker deployment position with a retainment mechanism; and expelling the marker out of a marker exit positioned proximate a distal end of the cannula.

Parts List

| Part Names | Number |
|---|---|
| delivery device | 10 |
| hub | 11 |
| cannula | 12 |
| grip | 16 |
| actuator | 18 |
| plunger | 20 |
| rod | 22 |
| depression portion | 24 |
| retainment tabs | 26a |
| retainment tabs | 26b |
| upper rim | 28 |
| chamfered edge | 30 |

-continued

Parts List

| Part Names | Number |
|---|---|
| marker delivery device | 100 |
| hub | 111 |
| cannula | 112 |
| grip | 116 |
| actuator | 118 |
| plunger | 120 |
| rod | 122 |
| retainment arms | 126 |
| retainment arms | 126a |
| retainment arms | 126b |
| angled portion | 128a |
| angled portion | 128b |
| grasping portion | 129a |
| grasping portion | 129b |
| channel | 130 |
| marker delivery device | 200 |
| hub | 211 |
| cannula | 212 |
| grip | 216 |
| actuator | 218 |
| plunger | 220 |
| rod | 222 |
| retainment arms | 226a |
| retainment arms | 226b |
| angled portion | 228a |
| angled portion | 228b |
| grasping portion | 229a |
| grasping portion | 229b |
| channel | 230 |
| marker delivery device | 300 |
| hub | 311 |
| cannula | 312 |
| grip | 316 |
| actuator | 318 |
| plunger | 320 |
| rod | 322 |
| retainment arms | 326a |
| retainment arms | 326b |
| angled portion | 328a |
| angled portion | 328b |
| grasping portion | 329a |
| grasping portion | 329b |
| channel | 330 |
| lip | 332 |
| marker delivery device | 400 |
| hub | 411 |
| cannula | 412 |
| grip | 416 |
| actuator | 418 |
| plunger | 420 |
| rod | 422 |
| detent | 426 |
| rib | 430 |
| device | 500 |
| operative end | 502 |
| deployment end | 504 |
| side opening | 506 |
| marker | 508 |
| tip | 510 |
| lumen | 511 |
| cannula | 512 |
| ramp | 514 |
| rod | 516 |

Figure 1:
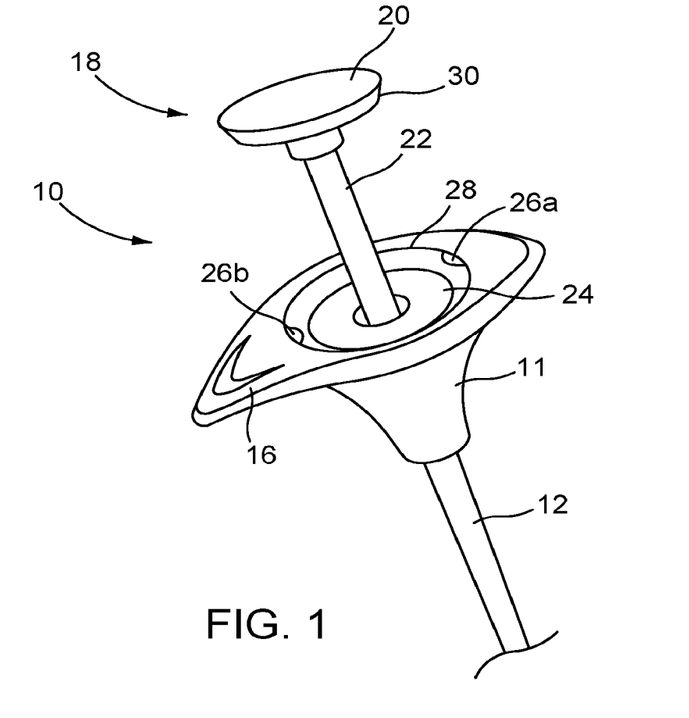
FIG. 1 is a perspective view of an example marker delivery device in a pre-actuated state in accordance with aspects of the present invention.
Figure 2:
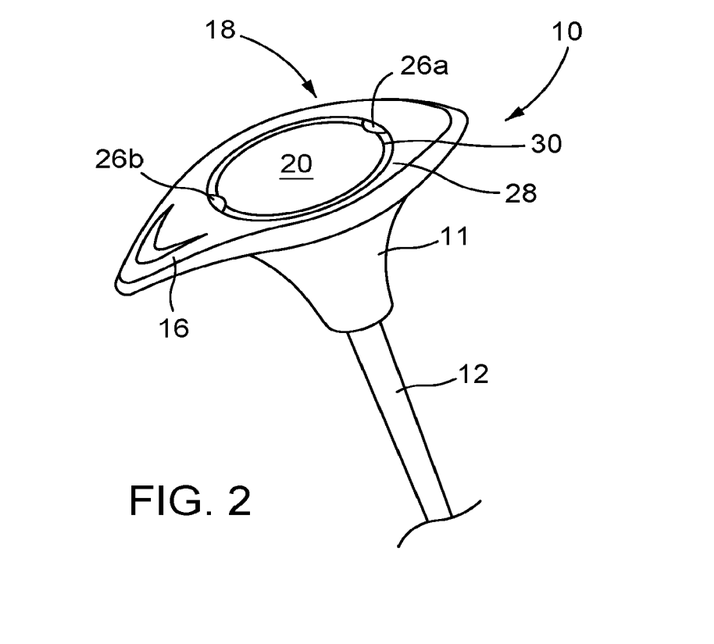
FIG. 2 is a perspective view of the example marker delivery device of FIG. 1 in a post-actuated state.

FIGS. 1 and 2 illustrate the operative end 502 (labeled and shown in detail in FIG. 17) of marker delivery device 10 which includes an elongate outer cannula 12. Operative end 502 is the end of marker delivery device 10 that the operator directly manipulates. While not shown in FIGS. 1 and 2 (see FIG. 17), the cannula has a marker exit, shown as side opening 506 formed adjacent to, but spaced proximally from, the distal end of the cannula 12.

A hub 11 including a grip 16 may be provided at the proximal end of cannula 12. An actuator 18 can be provided, with the actuator 18 extending coaxially in cannula 12 such that actuator 18 is configured to translate within cannula 12 to displace one or more markers through side or other opening (not shown in FIGS. 1 and 2, see FIG. 17). The actuator 18 may include a plunger 20 coupled with a rod 22. The rod 22 may have sufficient rigidity in compression to push a marker from an internal lumen of the cannula 12 out through opening. The rod 22 may also be relatively flexible in bending to allow the rod 22 to bend toward the opening in some embodiments. The plunger 20 may be coupled at the proximal end of rod 22 for forcing rod 22 distally in cannula 12 to deploy a marker out of cannula 12.

A user may grasp grip 16 with two fingers of one hand, and may push on plunger 20 using the thumb on the same hand, so that marker delivery device 10 is operated by a user's single hand. A spring (not shown) or other feature may be provided about rod 22 to bias rod 22 proximally relative to grip 16 and cannula 12.

The cannula 12 may be formed of any suitable metallic or non-metallic material. In some versions, the cannula 12 is formed of a thin walled hollow tube formed of a suitable medical grade plastic or polymer. One suitable material is a thermoplastic elastomer, such as Polyether block amide (PEBA), such as is known under the tradename PEBAX. The cannula 12 may be formed of PEBAX, and may be substantially transparent to visible light and X-ray. One suitable material is a thermoplastic elastomer, such as Polyether block amide (PEBA), available commercially for sale under the tradename PEBAX, see http://www.pebax.com/en/pebax-range/product-viewer/Pebaxsup-sup-00001/. The rod 22 may be formed of the same or different materials. These materials, among others, are applicable to all of the various example aspects disclosed herein.

The manner in which the rod 22 expels the marker, and more particularly, the structure of the deployment end of the device (including the opening) may be any suitable structure found in any known marker deployment devices. That is, the actuator retainment features described herein are applicable to any type of marker deployment device in which a plunger 20 is used to expel the marker. For example, the sliding of the rod 22 within the cannula 12 to deploy a marker may be as disclosed in any of the above-noted references (e.g., U.S. Pat. Nos. 6,371,904; 6,993,375; 6,996,433; 7,044,957; 7,047,063; 7,229,417; 7,465,279; 8,068,895; 8,241,299; 8,371,443; 8,414,602, and U.S. Published Patent Numbers 2014/0276037, now abandoned and 2013/0237912; all of these US Patents and Published Patent applications being incorporated by reference, in their entirety).

In one invention, as described in U.S. Pub. No. 2014/0276037, the side opening may be formed by cutting away a portion of the wall of cannula 12. The side opening may communicate with an internal lumen of cannula 12. The side opening may extend axially (in a direction parallel to the axis of lumen) from a proximal opening end to a distal opening end. Additionally, as described in 2014/0276037, the distal tip may extend from the distal end of the cannula 12 and may be rounded. The distal end of the cannula may be closed by a unitary endpiece, with a portion of the endpiece extending into internal lumen of cannula 12. The endpiece may include a tip, a ramp having a ramp surface, and a marker engaging element (or other features such as an ejection spring with or without a ramp). The ramp surface may aid in directing marker from internal lumen through side opening. The marker engaging element may help to retain the marker in the internal lumen until the user intends to deploy marker. While the above structure is one example of the deployment features (specifically as described in shown in 2014/0276037), as noted above, the deployment features of any of the above-listed references may be implemented. Furthermore, these various deployment features, among others, are applicable to all of the various example aspects disclosed herein.

The hub 11 may further include a depression portion 24 that defines a space corresponding to the shape of the plunger 20. For example, as shown in FIG. 1, the depression portion 24 may define an oval shape that is congruent with the oval shape of the plunger 20. Other suitable shapes may be used, for example shapes that are intuitively actuated by a human finger/thumb, such as circular, elliptical, and oblong shapes, among others. The hub 11 may further include one or more retainment tabs 26a, 26b (interchangeably referred herein as a retainment mechanism). As shown in FIG. 1 the retainment tabs may be disposed on opposite ends of the depression portion 24. More particularly, the retainment tabs 26a, 26b may extend from an upper rim 28 of the hub 11 that defines the depression portion 24. While two tabs 26a, 26b are illustrated, only one or more than two (e.g., three, four, five, etc.) may be implemented. The plunger 20 may further include a chamfered edge 30. The chamfered edge 30 may correspond to the retainment tabs 26a, 26b, so as to engage with the retainment tabs 26a, 26b when the plunger 20 is depressed and fully inserted into the depression portion 24. The retainment tabs 26a, 26b may be sufficiently resilient to bend or compress when a force is applied, but then return to their original extended state once the force is removed.

To operate the delivery device 10, the operator may grasp grip 16 with two fingers of one hand, and may push on plunger 20 using the thumb on the same hand, as described above. As the operator continues to apply pressure on the plunger, the rod 22 will travel within the cannula 12 toward the distal end of the cannula. As the actuation continues the plunger 20 gets closer to entering the depression portion 24. When the underside of the plunger 20 reaches the retainment tabs 26a, 26b, the continued application of force against the retainment tabs 26a, 26b will cause the retainment tabs 26a, 26b to bend or compress. With the retainment tabs 26a, 26b retracted or compressed continued application of force on the plunger 20 allows the plunger to continue travel into the depression portion 24. FIG. 2 shows the delivery device 10 in a fully actuated state where the plunger 20 has been completely pushed into the depression portion 24. As shown in FIG. 2, once the plunger 20 is fully inserted into the depression portion 24, the chamfered edge 30 of the plunger 20 is aligned with the retainment tabs 26a, 26b. Because of the resiliency of the retainment tabs 26a, 26b, the retainment tabs 26a, 26b will bias toward to their original position, which is now engaged with the chamfered edge 30. With the retainment tabs 26a, 26b engaging the chamfered edge 30, the plunger 20 is retained in place fully within the depression portion 24, thereby preventing movement of the plunger in a direction opposite the direction of actuation. Thus, once fully inserted and engaged, the plunger is retained in a fully actuated state so that the operator can feel and see that the plunger has been fully actuated and the marker is deployed.

Figure 3:
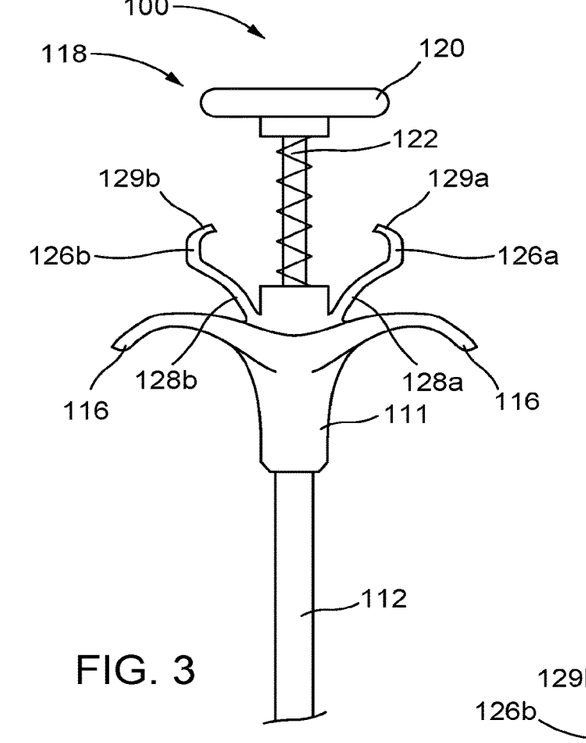
FIG. 3 is a side view of an example marker delivery device in a pre-actuated state in accordance with aspects of the present invention.
Figure 4:
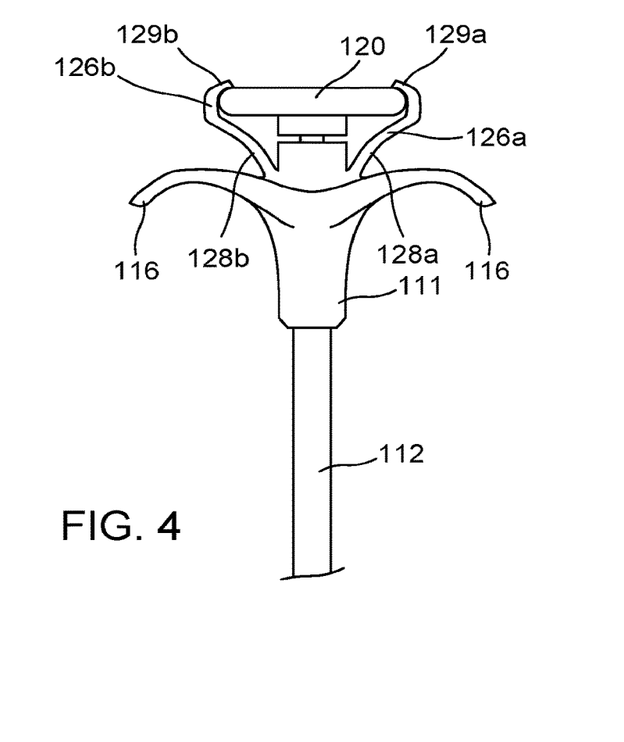
FIG. 4 is a side view of the example marker delivery device of FIG. 3 in a post-actuated state.
Figure 5:
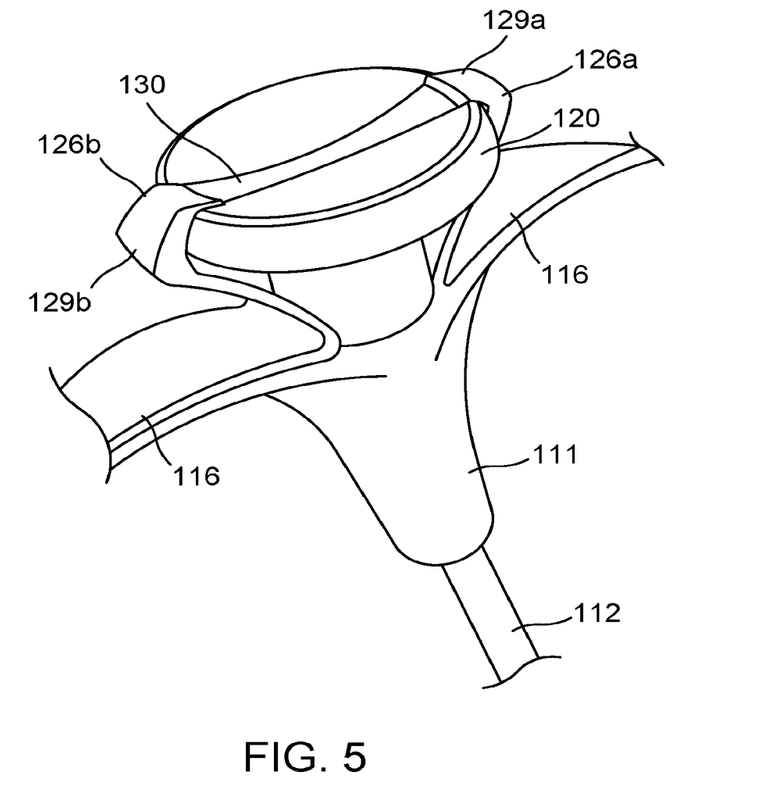
FIG. 5 is a perspective view of the example marker delivery device of FIG. 3 in a post-actuated state.
Figure 6:
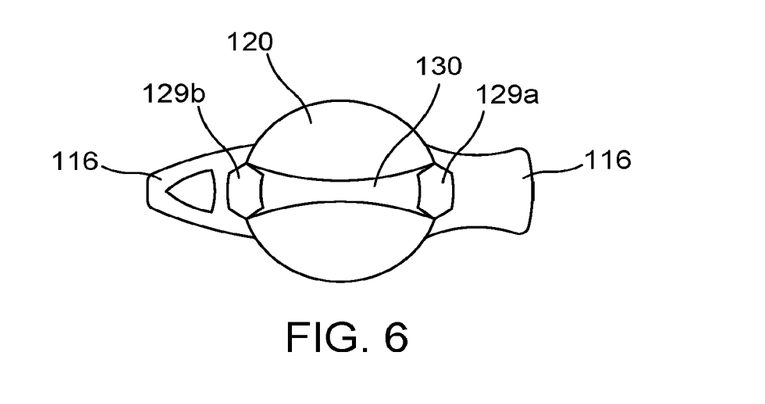
FIG. 6 is a plan view of the example marker delivery device of FIG. 3 in a post-actuated state.

FIGS. 3-6 show another example marker delivery device 100 in accordance with aspects of the present invention. FIG. 3 shows a side view of the marker delivery device 100 in a pre-actuated state. FIG. 4 shows a side view of the marker delivery device 100 in a post-actuated state. FIG. 5 shows a perspective view of the marker delivery device 100 in the post-actuated state. FIG. 6 shows a plan view of the marker delivery device 100 in the post-actuated state. The marker delivery device 100 includes similar feature as discussed above with respect to the marker delivery device 10 of FIGS. 1 and 2, and similar elements have similar reference numbers. The marker delivery device 100 may include an elongate outer cannula 112, a hub 111 including a grip 116 provided at the proximal end of cannula 112, and an actuator 118 including a plunger 120 coupled with a rod 122. These elements may operate in the same or similar manner as described above.

As shown in FIGS. 3-6, the marker delivery device 100, and more particularly, the hub 111, may include retainment arms 126a, 126, (interchangeably referred herein as a retainment mechanism). The retainment arms 126a, 126b may be disposed on opposite ends of the hub and may extend upwardly at an angle. While two retainment arms 126a, 126b are illustrated, only one or more than two (e.g., three, four, five, etc.) may be implemented. The plunger 120 may further include channel 130. The channel 130 may correspond to the retainment arms 126a, 126b, so as to engage with the retainment arms 126a, 126b when the plunger 120 is fully depressed. The retainment arms 126a, 126b may be sufficiently resilient to bend or spread when a force is applied, but then return to their original state once the force is removed. The retainment arms 126a, 126b may include an angled portion 128a, 128b, and a grasping portion 129a, 129b.

To operate the marker delivery device 100, the operator may grasp grip 116 with two fingers of one hand, and may push on plunger 120 using the thumb on the same hand, as described above. As the operator continues to apply pressure on the plunger, the rod 122 will travel within the cannula 112 toward the distal end of the cannula. As the actuation continues, the plunger 120 moves closer to contacting the hub 111. When the underside of the plunger 120 reaches the retainment arms 126a, 126b, the continued application of force against the retainment arms 126a, 126b, more particularly the grasping portions 129a, 129b, will cause the retainment arms 126a, 126b to expand or spread in a direction away from rod 122. With the retainment arms 126a, 126b expanded or spread, continued application of force on the plunger 120 allows the plunger to continue travel toward the hub 111 between the retainment arms 126a, 126b.

FIGS. 4-6 show the marker delivery device 100 in a fully actuated state where the plunger 120 has been completely depressed. As shown in FIGS. 4-6, once the plunger 120 is fully depressed, the channel 130 of the plunger 120 is aligned with the grasping portion 129a, 129b of the retainment arms 126a, 126b. Because of the resiliency of the retainment arms 126a, 126b, the retainment arms 126a, 126b will bias toward to their original position, in which the grasping portion 129a, 129b is now engaged with the channel 130. With the grasping portions 129a, 129b of the retainment arms 126a, 126b engaging the channel 130, the plunger 120 is retained in the fully depressed state, thereby preventing movement of the plunger in a direction opposite the direction of actuation. Thus, once fully engaged, the plunger is retained in a fully actuated state so that the operator can feel and see that the plunger has been fully actuated and the marker is deployed.

Figure 7:
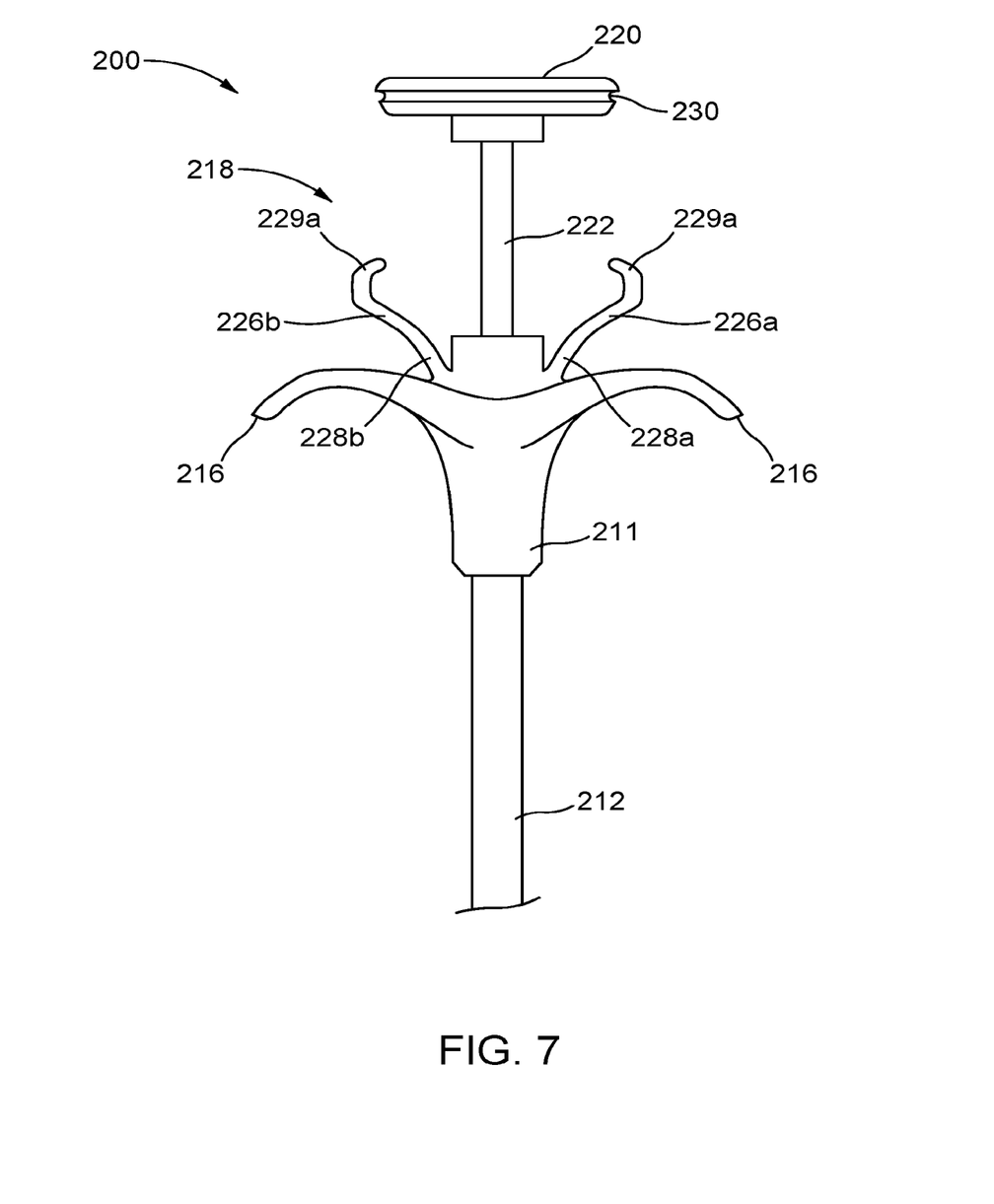
FIG. 7 is a side view of an example marker delivery device in a pre-actuated state in accordance with aspects of the present invention.
Figure 8:
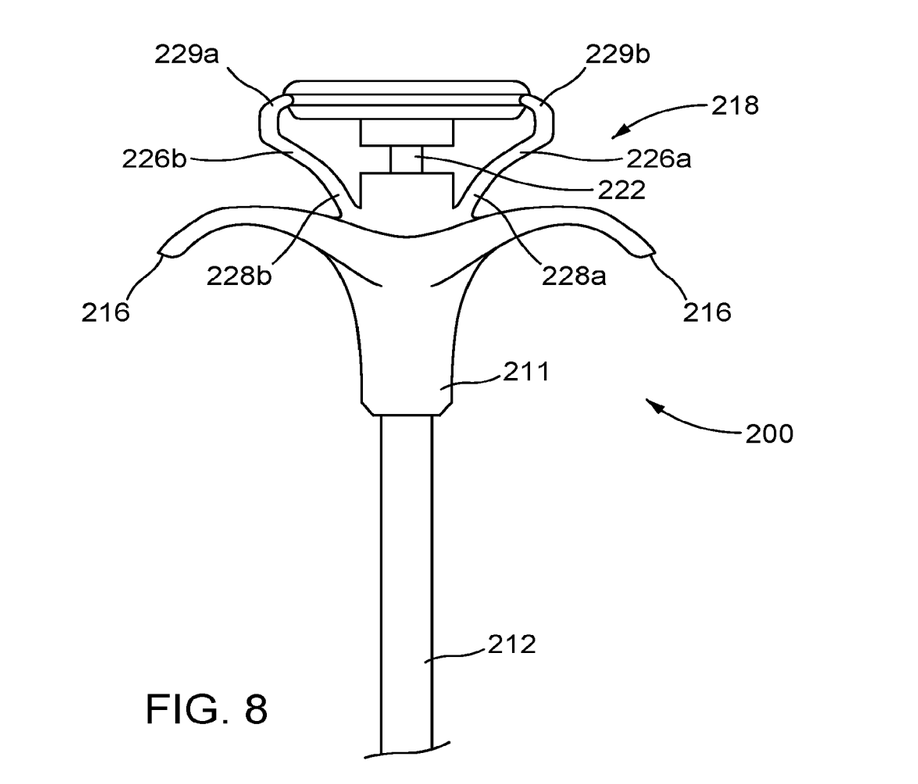
FIG. 8 is a side view of the example marker delivery device of FIG. 7 in a post-actuated state.
Figure 9:
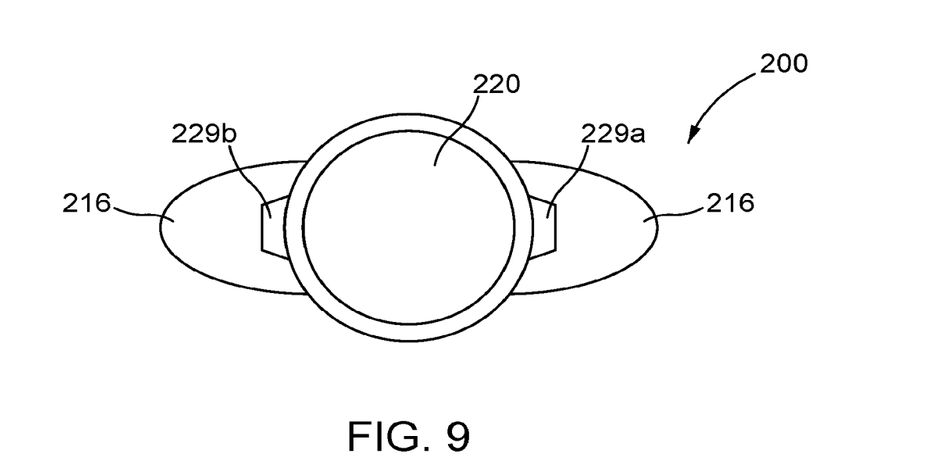
FIG. 9 is a plan view of the example marker delivery device of FIG. 7 in a post-actuated state.

FIGS. 7-9 show another example marker delivery device 200 in accordance with aspects of the present invention. FIG. 7 shows a side view of the marker delivery device 200 in a pre-actuated state. FIG. 8 shows a side view of the marker delivery device 200 in a post-actuated state. FIG. 9 shows a plan view of the marker delivery device 200 in the post-actuated state. The marker delivery device 200 includes similar features as discussed above with respect to the marker delivery device 10 of FIGS. 1 and 2, and similar elements have similar reference numbers. The marker delivery device 200 may include an elongate outer cannula 212, a hub 211 including a grip 216 provided at the proximal end of cannula 212, and an actuator 218 including a plunger 220 coupled with a rod 222. These elements may operate in the same or similar manner as described above.

As shown in FIGS. 7-8, the marker delivery device 200, and more particularly, the hub 211, may include retainment arms 226a, 226b, (interchangeably referred herein as a retainment mechanism). The retainment arms 226a, 226b may be disposed on opposite ends of the hub and may extend upwardly at an angle. While two retainment arms 226a, 226b are illustrated, only one or more than two (e.g., three, four, five, etc.) may be implemented. The plunger 220 may further include a channel 230 (interchangeably referred herein as a detent) extending circumferentially around a side surface of the plunger 220. The channel 230 may correspond to the retainment arms 226a, 226b, so as to engage with the retainment arms 226a, 226b when the plunger 220 is fully depressed. The retainment arms 226a, 226b may be sufficiently resilient to bend or spread when a force is applied, but then return to their original state once the force is removed. The retainment arms 226a, 226b may include an angled portion 228a, 228b, and a grasping portion 229a, 229b.

To operate the marker delivery device 200, the operator may grasp grip 216 with two fingers of one hand, and may push on plunger 220 using the thumb on the same hand, as described above. As the operator continues to apply pressure on the plunger, the rod 222 will travel within the cannula 212 toward the distal end of the cannula 212. As the actuation continues, the plunger 220 moves closer to contacting the hub 211. When the underside of the plunger 220 reaches the retainment arms 226a, 226b, the continued application of force against the retainment arms 226a, 226b, more particularly the grasping portions 229a, 229b, will cause the retainment arms 226a, 226b to expand or spread in a direction away from rod 222. With the retainment arms 226a, 226b expanded or spread, continued application of force on the plunger 220 allows the plunger 220 to continue travel toward the hub 211 between the retainment arms 226a, 226b. FIGS. 8 and 9 show the marker delivery device 200 in a fully actuated state where the plunger 220 has been completely depressed. As shown in FIGS. 8 and 9, once the plunger 220 is fully depressed, the channel 230 of the plunger 220 is aligned with the grasping portion 229a, 229b of the retainment arms 226a, 226b. Because of the resiliency of the retainment arms 226a, 226b, the retainment arms 226a, 226b will bias toward their original position, in which the grasping portion 229a, 229b is now engaged with the channel 230. With the grasping portions 229a, 229b of the retainment arms 226a, 226b engaging the channel 230, the plunger 220 is retained in the fully depressed state, thereby preventing movement of the plunger 220 in a direction opposite the direction of actuation. Thus, once fully engaged, the plunger 220 is retained in a fully actuated state so that the operator can feel and see that the plunger 220 has been fully actuated and the marker is deployed.

Figure 10:
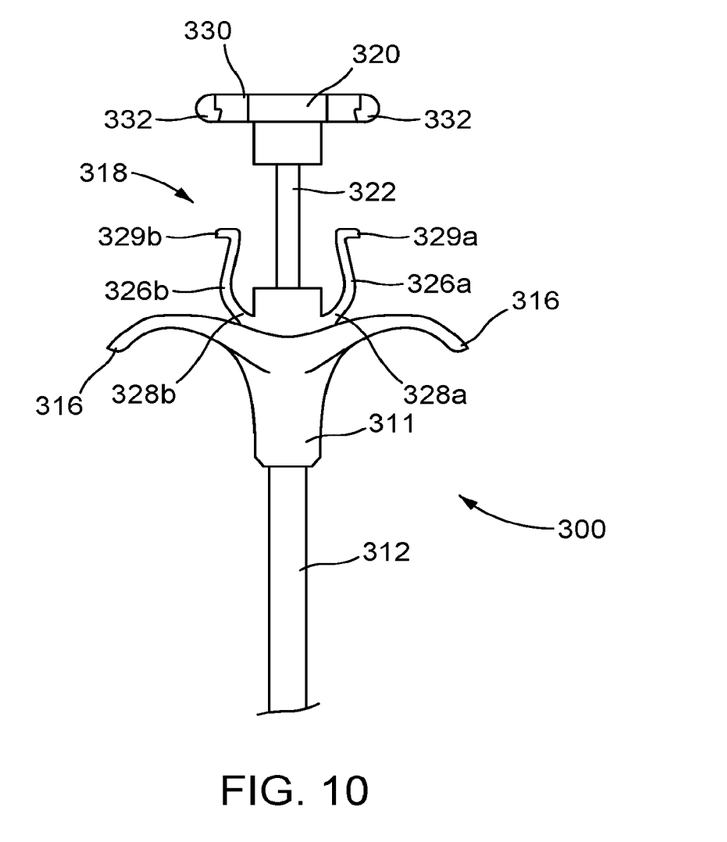
FIG. 10 is a side view of an example marker delivery device in a pre-actuated state in accordance with aspects of the present invention.
Figure 11:
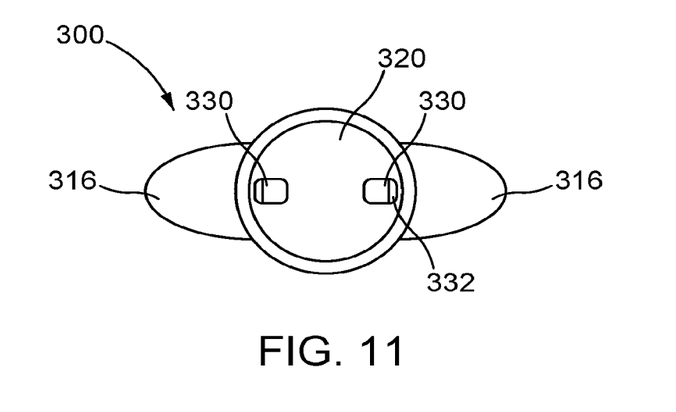
FIG. 11 is a plan view of the example marker delivery device of FIG. 10 in a pre-actuated state.
Figure 12:
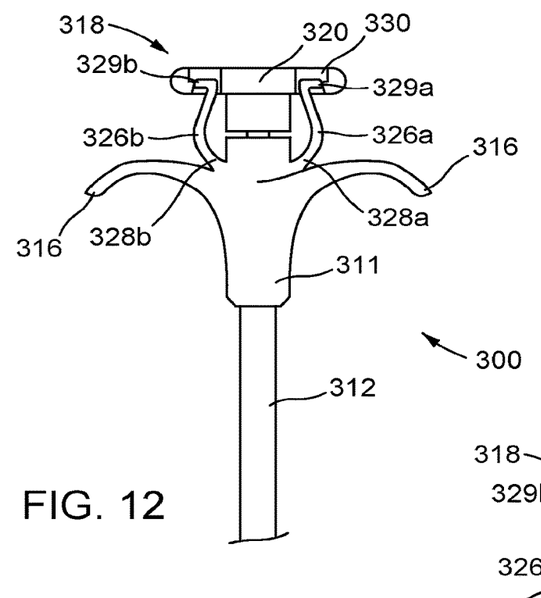
FIG. 12 is a side view of the example marker delivery device of FIG. 10 in a partially-actuated state.
Figure 13:
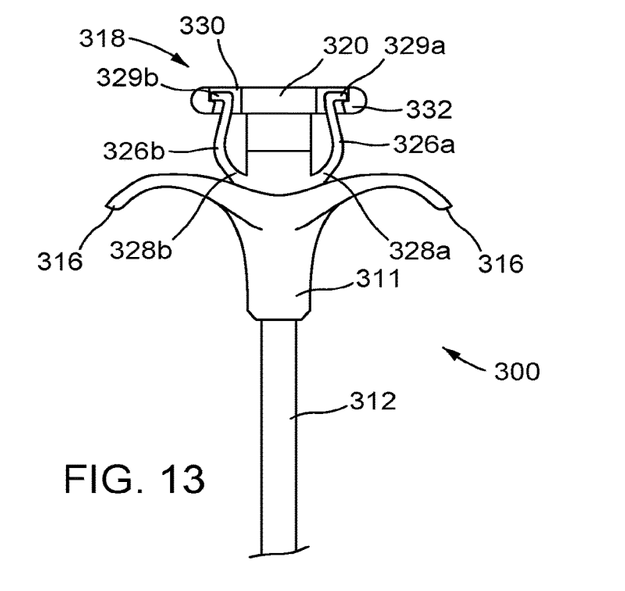
FIG. 13 is a side view of the example marker delivery device of FIG. 10 in a post-actuated state.
Figure 14:
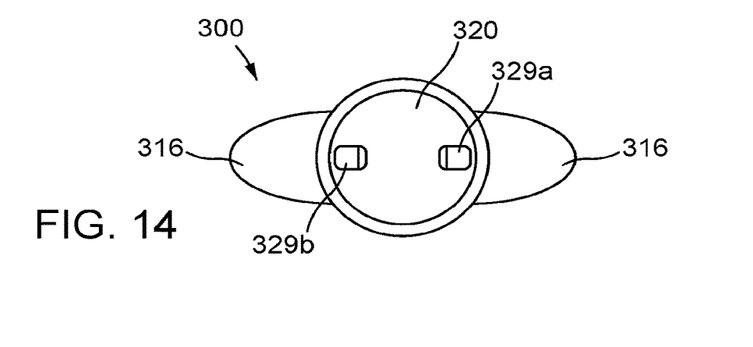
FIG. 14 is a plan view of the example marker delivery device of FIG. 10 in a post-actuated state.

FIGS. 10-14 show another example marker delivery device 300 in accordance with aspects of the present invention. FIG. 10 shows a side view of the marker delivery device 300 in a pre-actuated state. FIG. 11 shows a plan view of the marker delivery device 300 in the pre-actuated state. FIG. 12 shows a side view of the marker delivery device 300 in partially actuated state. FIG. 13 shows a side view of the marker delivery device 300 in a post-actuated state. FIG. 14 shows a plan view of the marker delivery device 300 in the post-actuated state. The marker delivery device 300 includes similar features as discussed above with respect to the marker delivery device 10 of FIGS. 1 and 2, and similar elements have similar reference numbers. The marker delivery device 300 may include an elongate outer cannula 312, a hub 311 including a grip 316 provided at the proximal end of cannula 312, and an actuator 318 including a plunger 320 coupled with a rod 322. These elements may operate in the same or similar manner as described above.

As shown in FIGS. 10-14, the marker delivery device 300, and more particularly, the hub 311, may include retainment arms 326a, 326b, (interchangeably referred herein as a retainment mechanism). The retainment arms 326a, 326b may be disposed on opposite ends of the hub and may extend upwardly at an angle. While two retainment arms 326a, 326b are illustrated, only one or more than two (e.g., three, four, five, etc.) may be implemented. The plunger 320 may further include an inner channel 330 extending circumferentially around an inner side surface of the plunger 320. The plunger 320 may further include a lip 332 that extends into the channel 330. The channel 330 and lip 332 may correspond to the retainment arms 326a, 326b, so as to engage with the retainment arms 326a, 326b when the plunger 320 is fully depressed. The retainment arms 326a, 326b may be sufficiently resilient to bend or retract when a force is applied, but then return to their original state once the force is removed. The retainment arms 326a, 326b may include an angled portion 328a, 328b, and a grasping portion 329a, 329b.

To operate the marker delivery device 300, the operator may grasp grip 316 with two fingers of one hand, and may push on plunger 320 using the thumb on the same hand, as described above. As the operator continues to apply pressure on the plunger 320, the rod 322 will travel within the cannula 312 toward the distal end of the cannula 312. As the actuation continues, the plunger 320 moves closer to contacting the hub 311. When the underside of the plunger 320 reaches the retainment arms 326a, 326b, the continued application of force against the retainment arms 326a, 326b, more particularly the grasping portions 329a, 329b, will cause the retainment arms 326a, 326b to bend or retract in a toward rod 322. With the retainment arms 326a, 326b bent or retracted, continued application of force on the plunger 320 allows the plunger 320 to continue travel toward the hub 311 between the retainment arms 326a, 326b. As shown in FIG. 11, prior to actuation, the grasping portions 329 and 329b of the retainment arms 326a and 326b are not engaged with the lip 332. FIGS. 12-14 show the marker delivery device 300 in a fully actuated state where the plunger 320 has been completely depressed. As shown in FIG. 12, just before complete actuation the grasping portions 329a, 329b of the retainment arms 326a, 326b have entered into the channel 330, and are abutting the side surface of the lip 332, but have not yet engaged the lip 332. At this state, the retainment arms 326a, 326b are being bent or retracted toward each other. As shown in FIGS. 12-14, once the plunger 320 is fully depressed, the lip 332 of the plunger 320 is aligned with the grasping portion 329a, 329b of the retainment arms 326a, 326b. Because of the resiliency of the retainment arms 326a, 326b, the retainment arms 326a, 326b will bias toward their original position, in which the grasping portion 329a, 329b is now engaged with the lip 332. With the grasping portions 329a, 329b of the retainment arms 326a, 326b engaging the lip 332, the plunger 320 is retained in the fully depressed state, thereby preventing movement of the plunger in a direction opposite the direction of actuation. Thus, once fully engaged, the plunger is retained in a fully actuated state so that the operator can feel and see that the plunger has been fully actuated and the marker is deployed.

Figures 15, 16:
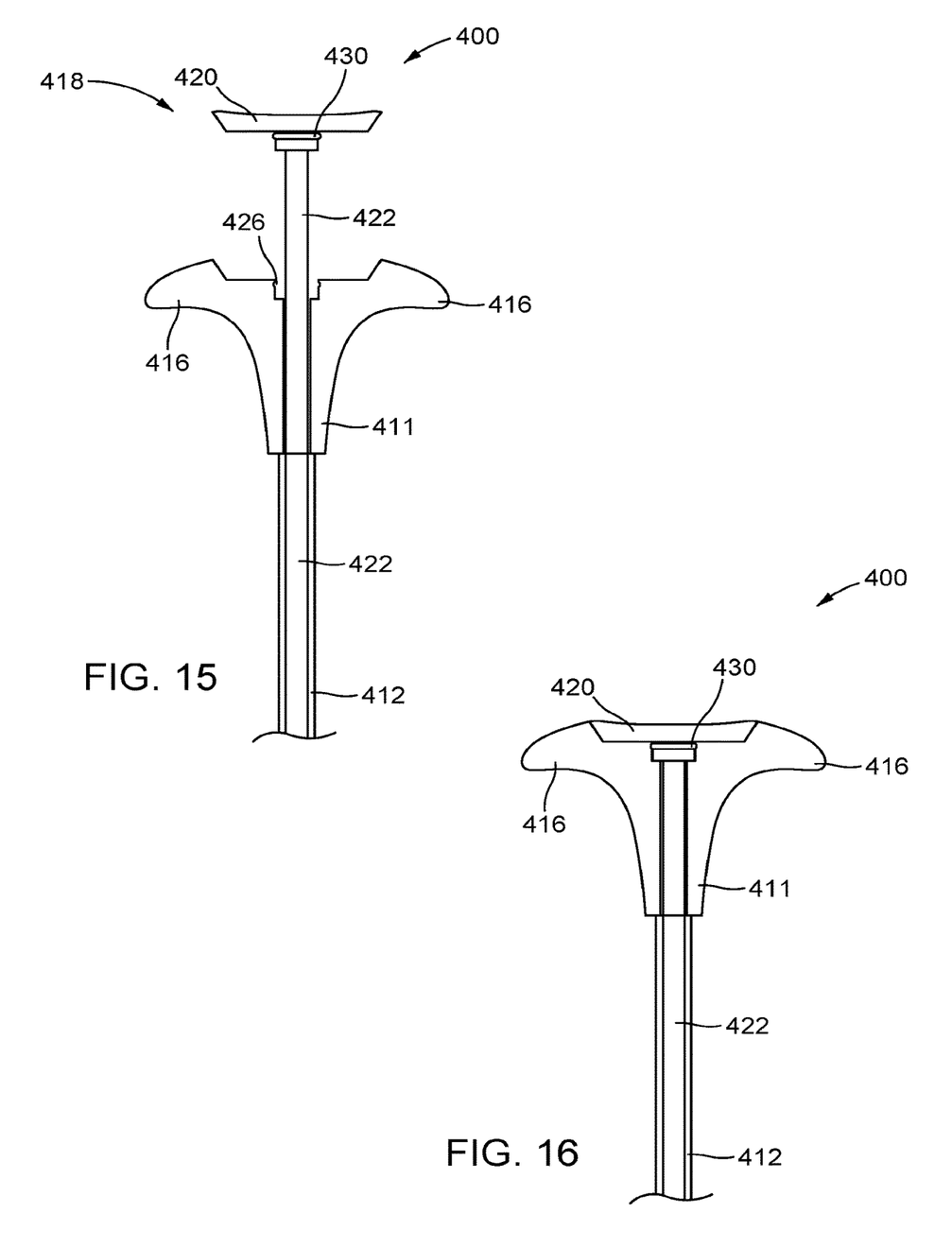
FIG. 15 is a side view of an example marker delivery device in a pre-actuated state in accordance with aspects of the present invention.
FIG. 16 is a side view of the example marker delivery device of FIG. 15 in a post-actuated state.

FIGS. 15 and 16 show another example marker delivery device 400 in accordance with aspects of the present invention. FIG. 15 shows a cross section view of the marker delivery device 400 in a pre-actuated state. FIG. 16 shows a cross section view of the marker delivery device 400 in a post-actuated state. The marker delivery device 400 includes similar features as discussed above with respect to the marker delivery device 10 of FIGS. 1 and 2, and similar elements have similar reference numbers. The marker delivery device 400 may include an elongate outer cannula 412, a hub 411 including a grip 416 provided at the proximal end of cannula 412, and an actuator 418 including a plunger 420 coupled with a rod 422. These elements may operate in the same or similar manner as described above.

As shown in FIGS. 15 and 16, the marker delivery device 400, and more particularly, the hub 411, may include a detent 426, (interchangeably referred herein as retainment mechanism). The detent 426 may extend circumferentially along an internal surface of the hub 411. While one detent 426 is illustrated, more than one (e.g., two, three, four, five, etc.) may be implemented. The plunger 420 may further include a rib 430 extending circumferentially around an outer surface of the plunger 420. The rib 430 may correspond to the detent 426, so as to engage with the detent when the plunger 420 is fully depressed. The rib 430 may be sufficiently resilient to bend or compress when a force is applied, but then return to its original state once the force is removed.

To operate the marker delivery device 400, the operator may grasp grip 416 with two fingers of one hand, and may push on plunger 420 using the thumb on the same hand, as described above. As the operator continues to apply pressure on the plunger, the rod 422 will travel within the cannula 412 toward the distal end of the cannula 412. As the actuation continues, the plunger 420 moves closer to contacting the hub 411. When the rib 430 reaches the hub 411, the continued application of force, will cause the rib 430 to bend or compress toward rod radially inwardly. With rib 430 bent or compressed, continued application of force on the plunger 420 allows the plunger 420 to continue travel toward the hub 411. FIG. 16 shows the marker delivery device 400 in a fully actuated state where the plunger 420 has been completely depressed. As shown in FIG. 16, once the plunger 420 is fully depressed, the rib 430 of the plunger 420 is aligned with the detent 426 of the hub 411. Because of the resiliency of the rib 430, the rib 430 will bias toward its original position, in which the rib 430 is now engaged with the detent 426. With the rib 430 engaging the detent 426, the plunger 420 is retained in the fully depressed state, thereby preventing movement of the plunger in a direction opposite the direction of actuation. Thus, once fully engaged, the plunger is retained in a fully actuated state so that the operator can feel and see that the plunger has been fully actuated and the marker is deployed.

For all of the above example aspects, where any male feature is shown mating with a female feature, it should be understood that a male/female reversal is also suitable. For example, the detent in FIGS. 15 and 16 may instead be a rib, while the rib in FIGS. 15 and 16 may instead be a detent.

The marker deployment device described herein may be used in conjunction with any suitable biopsy device known in the art used as part of a biopsy procedure. For example, the marker deployment device may be used in conjunction with any of the biopsy devices described in U.S. Pat. Nos. 5,526,822; 6,086,544; 6,626,849; 7,442,171; 7,938,786; 8,118,755; 9,095,326; 8,251,916; and 8,532,747.

Figure 17:
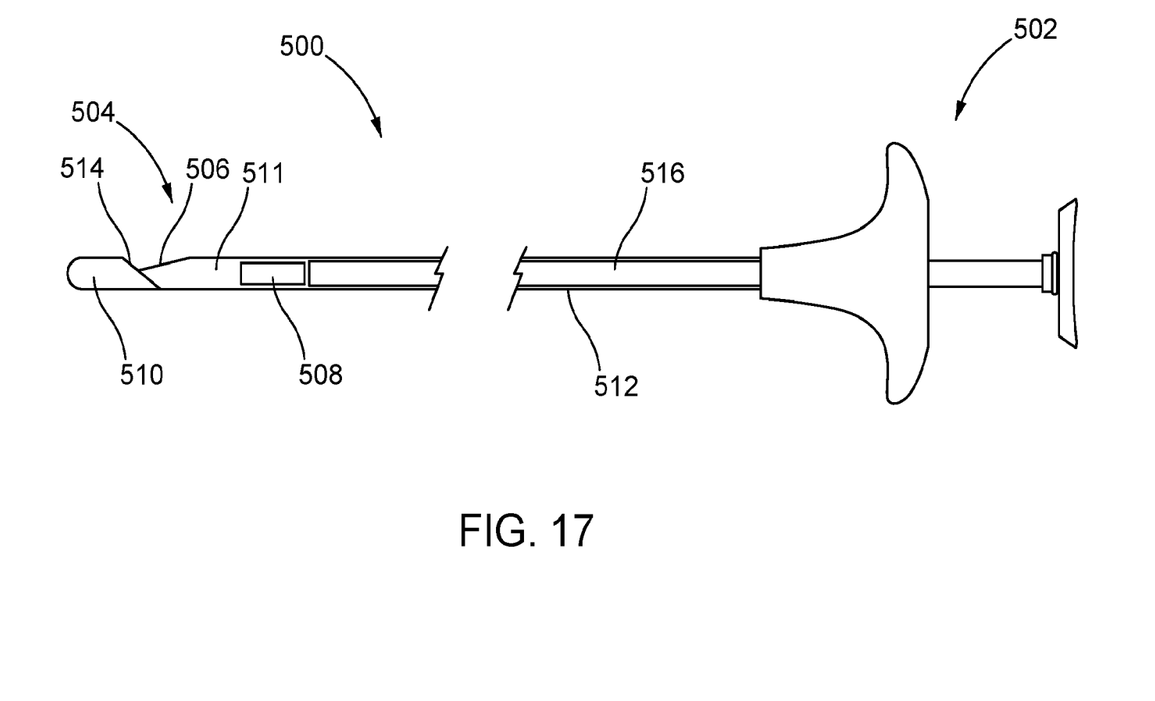
FIG. 17 is a side view of a marker delivery device in which the aspects of FIGS. 1-16 may be implemented.

FIG. 17 shows a side view of an example marker delivery device 500 in which the aspects of FIGS. 1-16 may be implemented. That is, an operative end 502 of the device 500 may include any of the features described above and shown in FIGS. 1-16. FIG. 17 additionally shows an example deployment end 504. As shown in FIG. 17, the deployment end 504 may include an opening 506 formed in the cannula 512. A marker 508 may be disposed within a lumen 511 of the cannula 512 prior to operation of the device. The cannula 512 may terminate in a tip 510. The tip 510 may include a ramp 514. As shown in FIG. 17, a rod 516 may be operatively connected with the operative end 502 and extend within the lumen 511 of the cannula 512. Once the operative end 502 is actuated (as described above with respect to any of FIGS. 1-16), the rod 516 pushes the marker 508 out of the opening 506.

The marker may be any suitable marker known in the art. For example, as described in U.S. Pat. No. 8,068,895 the marker may comprise a marker body and a marking element. In some versions, the marker body is visible under ultrasound imaging, while the marking element is visible under MRI and X-ray, among other imaging modalities. For instance, the marker body may be formed of polyethylene glycol hydrogel, bovine collagen, cellulose, beta glucan, Polylactic acid/Polyglycolide, Glycoprene® implantable grade polymers available from http://poly-med.com/services/implantable-grade-polymers-catalogue/glycoprene/, gelatinous materials such as hydrogel, and/or any other suitable material(s), including combinations thereof. Furthermore, the marker body may be biodegradable or bioabsorbable, or may have other properties. The marking element may comprise a titanium wire, pellet, or other structure. Any other material(s) may be used for the marking element, including combinations thereof. In some versions, the marker body is formed of a square collagen pad that is folded and/or rolled about a titanium the marking element to form a substantially cylindraceous marker. The marker is then compressed radially inward in this example before being inserted into the cannula for deployment. The marker may have a variety of alternative configurations, may be formed using a variety of techniques, and may be used in a variety of other ways as described in the other marker references incorporated by reference above.

While this invention has been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

The invention claimed is:

1. A marker delivery device, comprising:
a cannula including a distal end and a marker exit positioned proximate the distal end;
a hub extending from a proximal end of the cannula, the hub defining an open proximal end opposite the proximal end of the cannula;
an actuator movable to a marker deployment position, the actuator being slidably disposed within the cannula; and
a retainment mechanism configured to retain the actuator in the deployment position such that the actuator is secured in the deployment position once retained therein, a portion of the retainment mechanism extending from a portion of the hub, the retainment mechanism being partially exposed relative to the open proximal end of the hub to retain the actuator within the open proximal end, thereby blocking access to the actuator.

2. The marker delivery device of claim 1, the actuator including a plunger and a rod slidably disposed within the cannula to move to the marker deployment position via the plunger.

3. The marker delivery device of claim 1, the actuator including a plunger and a rod, the rod extending through the hub and being slidably disposed within the cannula to move to the marker deployment position, the hub defining a recess for receipt of the plunger therein.

4. The marker delivery device of claim 1, the actuator including a plunger and a rod, the rod extending through the hub and being slidably disposed within the cannula to move to the marker deployment position, the hub defining a recess for receipt of the plunger therein and one or more retainers proximate to the recess to retain the plunger in the deployment position.

5. The marker delivery device of claim 1, the actuator including a plunger and a rod, the rod extending through the handle hub and being slidably disposed within the cannula to move to the marker deployment position, the hub defining a recess for receipt of the plunger therein and one or more retainers proximate to the recess to retain the plunger in a position distal relative to a proximal face of the hub.

6. The marker delivery device of claim 1, the actuator including a plunger and a rod, the rod extends extending through the hub and being slidably disposed within the cannula to move to the marker deployment position, the hub defining a recess for receipt of the plunger therein and a retainer disposed in a lumen of the handle distally of the recess to retain the plunger in the deployment position.

7. The marker delivery device of claim 1, the actuator including one or more surface features configured to receive at least a portion of the retainment mechanism.

8. A marker delivery device, comprising:
(a) a cannula including a proximal end, a marker exit, and a lumen extending from the proximal end to the marker exit;
(b) a handle attached to the cannula at the proximal end;
(c) an actuator having plunger and a rod, the plunger and the rod being configured to move unitarily relative to the cannula to a deployment position for deploying a marker from the marker exit; and
(d) a one-way lock associated with the handle and configured to engage the plunger of the actuator to retain the plunger within the handle and the rod in the deployment position, a proximal face of the plunger being flush with a proximal face of the handle when the plunger is retained within the handle.

9. The marker delivery device of claim 8, the handle including a recess configured to receive the plunger of the actuator, the one-way lock including one or more tabs extending into the recess such that the one-way lock is configured to retain the plunger within the recess.

10. The marker delivery device of claim 8, the handle including a recess configured to receive the plunger of the actuator, the one-way lock including one or more tabs extending into the recess such that the one-way lock is configured to retain the plunger within the recess, the plunger including a chamfered edge corresponding to a chamfered interior of the recess.

11. A marker delivery device, comprising:
(a) a cannula including a proximal end, a marker exit, and a lumen extending from the proximal end to the marker exit;
(b) a hub attached to the cannula at the proximal end at a distal end of the hub, the hub including a proximal end and a recess defined in part by an upper rim and disposed within the proximal end;
(c) an actuator having plunger and a rod, the plunger and the rod being configured to move unitarily relative to the cannula to a deployment position for deploying a marker from the marker exit, the plunger defining a chamfered edge corresponding to a chamfered edge of the recess; and
(d) one or more retainment tabs extending into the recess of the hub from the upper rim and configured to engage the plunger to thereby retain the plunger within the recess of the hub when the actuator is moved to the deployment position, the one or more retainment tabs further being configured to retain a proximal surface of the plunger flush with the proximal end of the hub when the actuator is in the deployment position such that the hub is configured to block access to the plunger.

12. The marker delivery device of claim 11, the cannula further including a closed distal tip, the marker exit being proximate to the closed distal tip.

13. The marker delivery device of claim 11, the one or more retainment tabs including two retainment tabs.

14. The marker delivery device of claim 11, the actuator being coaxial with the cannula.

15. The marker delivery device of claim 11, the one or more retainment tabs including a first retainment tab and a second retainment tab, the first retainment tab extending from an opposite side of the hub relative to the second retainment tab.

16. The marker delivery device of claim 11, the one or more retainment tab having a resilient construction, the resilient construction being configured to bend when a predetermined force is applied, but return to an original configuration once the predetermined force is removed.

* * * * *